United States Patent [19]

Chandrakumar et al.

[11] Patent Number: 5,449,673

[45] Date of Patent: Sep. 12, 1995

[54] 10,11-DIHYDRO-10-(3-SUBSTITUTED-1-OXO-2-PROPYL, PROPENYL OR PROPYNYL)DIBENZ[B,F][1,4] OXAZEPINE PROSTAGLANDIN ANTAGONISTS

[75] Inventors: Nizal S. Chandrakumar, Vernon Hills; Timothy J. Hagen, Glenview; E. Ann Hallinan, Evanston; Robert K. Husa, Vernon Hills, all of Ill.

[73] Assignee: G. D. Searle & Co., Chicago, Ill.

[21] Appl. No.: 178,283

[22] PCT Filed: Aug. 13, 1992

[86] PCT No.: PCT/US92/06584

§ 371 Date: Jan. 10, 1994

§ 102(e) Date: Jan. 10, 1994

[87] PCT Pub. No.: WO93/07132

PCT Pub. Date: Apr. 15, 1993

[51] Int. Cl.[6] .................... A61K 31/55; C07D 267/20; C07D 413/12

[52] U.S. Cl. .................... 514/211; 540/547; 540/557

[58] Field of Search ................. 514/211; 540/547, 557

[56] References Cited

U.S. PATENT DOCUMENTS

| | | | |
|---|---|---|---|
| 2,852,528 | 9/1958 | Hoffmann et al. | 260/327 |
| 3,210,372 | 10/1965 | Werner et al. | 260/309.6 |
| 3,357,998 | 12/1967 | Cusic et al. | 260/333 |
| 3,534,019 | 10/1970 | Coyne et al. | 260/239 |
| 3,624,104 | 11/1971 | Cusic et al. | 260/333 |
| 3,917,649 | 11/1975 | Mueller | 260/333 |
| 3,989,719 | 11/1976 | Mueller | 260/333 |
| 3,992,375 | 11/1976 | Mueller | 260/240 |
| 4,045,442 | 8/1977 | Mueller | 260/293.58 |
| 4,125,532 | 11/1978 | Mueller | 260/244.4 |
| 4,170,715 | 10/1979 | Mueller | 260/243.3 |
| 4,290,953 | 9/1981 | Koizumi et al. | 260/333 |
| 4,379,150 | 4/1983 | Ito et al. | 424/244 |
| 4,559,336 | 12/1985 | Mueller | 514/211 |
| 4,559,337 | 12/1985 | Mueller | 514/211 |
| 4,614,617 | 9/1986 | Mueller | 540/547 |
| 4,681,939 | 7/1904 | Mueller | 540/547 |
| 4,704,386 | 11/1987 | Mueller | 514/211 |

(List continued on next page.)

FOREIGN PATENT DOCUMENTS

| | | | |
|---|---|---|---|
| 0012385 | 6/1980 | European Pat. Off. | C07D 267/20 |
| 0193822 | 9/1986 | European Pat. Off. | C07D 267/20 |
| 0218077 | 4/1987 | European Pat. Off. | C07D 267/20 |
| 0480641 | 4/1992 | European Pat. Off. | C07D 223/20 |

(List continued on next page.)

OTHER PUBLICATIONS

A. Bennett, et al. "Antagonism of Prostanoid-Induced Contractions of Rat Gastric Fundus Muscle by SC-19220 Sodium Meclofenamate, Indomethacin or Trimethoquinol," *Br. J. Pharmac.*, 71, 169–175 (1980)—London.

W. E. Coyne, et al. "Anticonvulsant Semicarbazides,"

(List continued on next page.)

*Primary Examiner*—Yogendra N. Gupta
*Attorney, Agent, or Firm*—Roberta L. Hastreiter; Roger A. Williams

[57] ABSTRACT

The present invention provides substituted dibenzoxazepine compounds of Formula I:

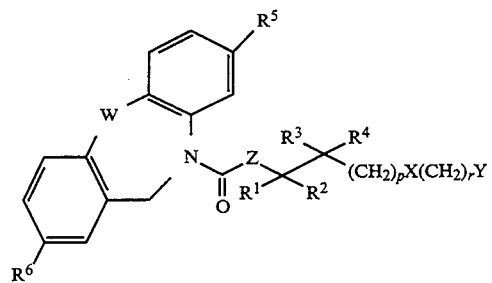

Formula I which are useful as analgesic agents for the treatment of pain, pharmaceutical compositions comprising a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

17 Claims, No Drawings

U.S. PATENT DOCUMENTS

| | | | |
|---|---|---|---|
| 5,180,720 | 1/1993 | Husa et al. | 514/211 |
| 5,182,272 | 1/1993 | Hallinan et al. | 514/211 |
| 5,212,169 | 5/1993 | Husa et al. | 514/211 |
| 5,225,417 | 7/1993 | Dappen et al. | 514/279 |
| 5,281,590 | 1/1994 | Husa et al. | 514/211 |
| 5,283,240 | 2/1994 | Hallinan et al. | 514/80 |
| 5,288,719 | 2/1994 | Husa et al. | 514/211 |

FOREIGN PATENT DOCUMENTS

| | | | |
|---|---|---|---|
| 0534667 | 3/1993 | European Pat. Off. | C07D 417/06 |
| 6700603 | 7/1967 | Netherlands . | |
| 1170322 | 11/1969 | United Kingdom | C07D 87/54 |
| 1331892 | 9/1973 | United Kingdom | C07D 87/54 |
| 1522003 | 8/1978 | United Kingdom | C07I 267/20 |
| 92/06584 | 8/1992 | WIPO . | |
| 92/08103 | 9/1992 | WIPO . | |
| 92/03028 | 11/1992 | WIPO | C07D 413/12 |

OTHER PUBLICATIONS

*J. Med. Chem.*, 11(6), 1158–1160 (1968)–USA.

E. J. Drower, et al. "The Antiociceptive Effects of Prostaglandin Antagonists in the Rat," *European Journal of Pharmacology*, 133, 249–256 (1987)–Europe.

F. R. George, et al. "Antagonism of Alcohol Hypnosis by Blockade of Prostaglandin Synthesis and Activity: Genotype and Time Course Effects," *Pharmacology, Biochemistry & Behavior*, vol. 19, 131–136 (1983)–USA.

R. Gimet, et al. "Quantitative Determination of Polymorphic Forms in a Formulation Matrix Using the Near Infra–Red Reflectance Analysis Technique," *Journal of Pharmaceutical & Biomedical Analysis*, vol. 5, No. 3, 205–211 (1987)–Great Britain.

A. Gomes, et al. "Pharacodynamics of Venom of the Centipede *Scolopendra Subspinipes Dehaani*," *Indian Journal of Experimental Biology*, vol. 20, 615–618, Aug. (1982)–India.

K. Gyires, et al. "The Use of the Writhing Test in Mice for Screening Different Types of Analgesics," *Arch. Int. Pharmacodyn*, 267, 131–140 (1984)–USA.

D. E. MacIntyre, et al. "Antagonism of Human Platelet Responses to Stimulatory and Inhibitory Prostaglandins," *Prog. Lipid. Res.*, 20(1–4), 453–9(1981)–USA.

C. A. Maggi, et al. "The Effect of SC–19220, a Prostaglandin Antagonist, on the Micturition Reflex in Rats," *European Journal of Pharmacology*, 152, 273–279 (1988)–Europe.

K. Nagarajan, et al. "Synthesis of 10,11–Dihydrodibenz[b,f][1,4]oxazepine Derivatives as Potential Anticonvulsant & Psychotropic Agents," *Indian Journal of Chemistry*, vol. 24B, 840–844(1985)–India.

S. Nakajyo, et al. "Inhibitory Effect of Bassianolide, a Cyclodepsipeptide, on Drug–Induced Contractions of Isolated Smooth Muscle Preparations," *Japan J. Pharmacol.*, 32, 55–64 (1982)–Japan.

A. Rakovska, et al. "Antagonistic Effect of SC–19220 on the Responses of Guinea–Pig Gastric Muscles to Prostaglandins $E_1$, $E_2$, and $F_{2\alpha}$," *Arch. Int. Pharmacodyn.*, 268, 59–69 (1984)–USA.

J. H. Sanner "Dibenzoxazepine Hydrazides as Prostaglandin Antagonists," *Intra–Science Chem. Rept.*, vol. 6, No. 1, 1–9 (1972)–USA.

J. H. Sanner, et al. "Structure–Activity Relationships of Some Dibenzoxazepine Derivatives as Prostaglandin Antagonists," *Advances in the Biosciences*, 9, 139–148 (1972)–USA.

10,11-DIHYDRO-10-(3-SUBSTITUTED-1-OXO-2-PROPYL, PROPENYL OR PROPYNYL)DIBENZ[B,F][1,4] OXAZEPINE PROSTAGLANDIN ANTAGONISTS

BACKGROUND OF THE INVENTION (1) Field of the Invention

This application is a 371 of PCT/U.S.92/06584, filed on Aug. 13, 1992.

The present invention generally relates to compounds having pharmacological activity which are useful as pharmacological agents and, more particularly, as analgesic agents for the treatment of pain, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and methods of treating pain employing these compounds.

Analgesic compounds are agents which alleviate pain without causing a loss of consciousness and, thus, which are useful for treating pain.

The major classes of analgesic compounds include narcotic analgesics, or opiates, compounds which alleviate pain and induce sleep, and analgesic-antipyretic compounds, compounds which alleviate pain and reduce fever, such as salicylates.

Although the efficacy of opiates in relieving pain is well established, the associated addiction liability of opiates is a distinct disadvantage of these compounds.

While salicylate and salicylate-like agents (non-steroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are neither opiates nor NSAIDS, and represent another class of compounds which are useful as analgesic agents.

(2) Description of the Related Art

U.S. Pat. No. 4,290,953 discloses dibenzoxazapine derivatives as-cholesterol lowering agents.

U.S. Pat. Nos. 4,559,336 and 4,614,617 (a continuation-in-part of U.S. 4,559,336) disclose 8-chlorodibenz[b,f][1,4] oxazepine-10(11H)-carboxylic acid, 2-(sulfinyl- and sulfonyl-containing acyl)hydrazides, and intermediates thereof.

U.S. Pat. No. 3,534,019 discloses hydrazides of dibenzoxazepine-, dibenzothiazepine- and dibenzodiazepine-carboxylic acids.

U.S. Pat. No. 3,624,104 discloses aralkanoyl derivatives of dibenzoxazepine-N-carboxylic acid hydrazide compounds.

U.S. Pat. No. 3,989,719 discloses N,N'-diacyl hydrazines.

U.S. Pat. Nos. 3,917,649 and 3,992,375 (a divisional of U.S. Pat. No. 3,917,649) disclose dibenzoxazepine N-carboxylic acid hydrazides compounds.

U.S. Pat. Nos. 4,045,442, 4,125,532 (a divisional of U.S. Pat. No. 4,045,442) and 4,170,593 (a divisional of U.S. Pat. No. 4,125,532) disclose 1(substituted amino)alkanoyl-2-(dibenzoxazepine-10-carbonyl)hydrazides compounds.

U.S. Pat. No. 4,559,337 discloses 8-chlorodibenz[b,f][1,4]-oxazepine-10(11H)-carboxylic acid, 2-(alkoxy-containing acyl)hydrazide compounds.

GB 1 522 003 discloses 1-acyl-2-(8-chloro-10,11-dihydrodibenz[b,f][1,4]oxazepine-10-carbonyl)hydrazine compounds.

GB 1 331 892 discloses derivatives of dibenzoxazepine N-carboxylic acid hydrazides.

European Patent Application Publication No. 0 193 822 discloses 8-chlorodibenz[b,f][1,4]-oxazepine-10(11H)-carboxylic acid, 2-(thio-, sulfinyl- and sulfonyl-containing acyl)hydrazide compounds.

European Patent Application Publication No. 0 218 077 discloses 8-chlorodibenz[b,f][1,4]oxazepine-10(11H)-carboxylic acid, 2[(substituted phenylsulfinyl)alkanoyl]hydrazide compounds and 8-chlorodibenz[b,f][1,4]oxazepine-10(11H)-carboxylic acid, 2-[(substituted phenylsulfonyl)alkanoyl]hydrazide compounds, and intermediates used in the preparation of these compounds.

Drower et al., "The Antiociceptive Effects of Prostaglandin Antagonists in the Rat," *European Journal of Pharmacology*, 133, 249–256 (1987), disclose the study of the antinociceptive properties of two competitive antagonists of prostaglandins of the E series, 8-chlorodibenz[b,f][1,4]-oxazepine-10(11H)-carboxylic acid, 2-acetylhydrazide and 8-chlorodibenz[b,f][1,4]-oxazepine-10(11H)-carboxylic acid, 2-(5-chloro-1-oxopentyl)hydrazide.

J. H. Sanner, "Dibenzoxazepine Hydrazides as Prostaglandin Antagonists," *Intra-Science Chem. Rept.*, 6(1), 1–9 (1972), describes experiments performed with two dibenzoxazepine derivatives designated SC-18637 and SC-19220, and shown below, and found that SC-18637 and SC-19220 inhibit the stimulant actions of prostaglandins on isolated smooth muscle preparations.

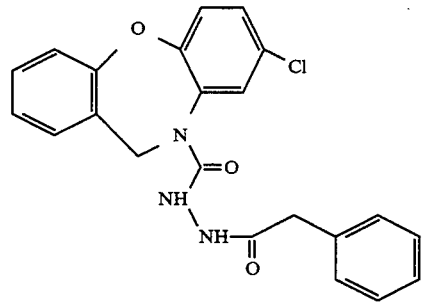

SC-18637

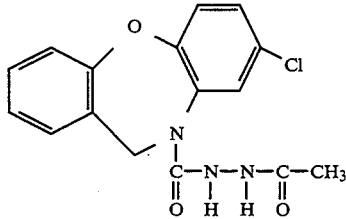

SC-19220

K. Nagarajan et al., "Synthesis of 10,11-Dihydrodibenz[b,f][1,4]oxazepine Derivatives as Potential Anticonvulsants & Psychotropic Agents," *Indian Journal of Chemistry*, 24B, 840–844 (1985), disclose the synthesis of acyl, carbamoyl and thiocarbamoyl derivatives of 10,11-dihydrodibenz[b,f][1,4]oxazepine, most of which have either a nitro or an amino group at position-2, as analogues of carbamazepine, and the evaluation of these derivatives as anticonvulsants associated with neuroleptic activity.

Other art which relates to the present invention includes that which is discussed below.

D. E. MacIntyre et al., "Antagonism of Human Platelet Responses to Stimulatory and Inhibitory Prostaglandins," *Prog. Lipid. Res.*, 20(1–4), 453–9 . (1981), disclose on Page 454, Lines 11–12, Page 458, Lines 43–44, and in Table 1, two dibenzoxazepine compounds designated SC-19220 and SC-25191, and shown above and below, respectively, which were employed in an investigation of the effects of prostaglandin antagonists on platelet responses to stimulatory and inhibitory prostaglandins.

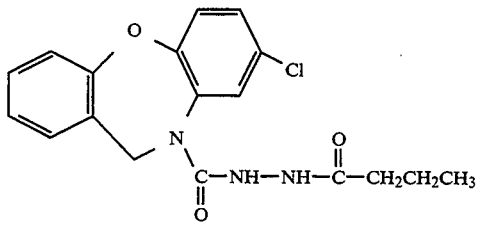

SC-25191

R. Gimet et al., "Quantitative Determination of Polymorphic Forms in a Formulation Matrix Using the Near Infra-Red Reflectance Analysis Technique," *J. Pharmaceutical & Biomedical Analysis*, 5(3), 205–211 (1987), disclose an analytical method for the determination of the polymorphic transformation of an active ingredient in a solid dosage form matrix, and discuss a compound designated SC-25469, and shown below, at Page 206, Lines 16–23.

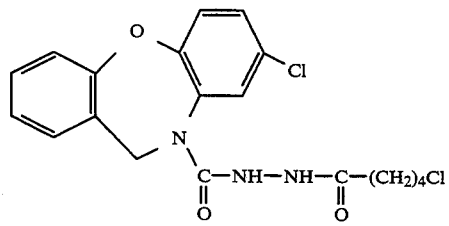

SC-25469

J. H. Sanner et al., "Structure-Activity Relationships of some Dibenzoxazepine Derivatives as Prostaglandin Antagonists," *Advances in the Biosciences*, 2, 139–148 (1972), disclose tests for prostaglandin antagonism on isolated guinea-pig ileum and rat stomach fundus strips with the n-butanoyl, i-butanoyl and n-hexanoyl analogs of SC-19220 (see structure above) and, on Page 140, Lines 11–18, show the chemical structures of the compounds used in the study.

A. Rakovska et al., "Antagonistic Effect of SC-19220 on the Responses of Guinea-Pig Gastric Muscles to Prostaglandins E$_1$, E$_2$ and F$_2$," *Arch. int. Pharmacodyn*, 268, 59–69 (1984), disclose a study of the contractile responses of guinea-pig gastric muscles to SC-19220 (see structure above), and the prostaglandin-blocking activity and specificity of SC-19220 on these muscles.

W. E. Coyne et al., "Anticonvulsant Semicarbazides," *J. Med. Chem.*, 11(6), 1158–1160 (1968), disclose the investigation of the structureactivity relationship of the anticonvulsant activity of a series of semicarbazides which was synthesized from various tricyclic amines (see Table I, Page 1160).

K. Gyires et al., "The Use of the Writhing Test in Mice for Screening Different Types of Analgesics," *Arch. int. Pharmacodyn*, 267, 131–140 (1984), describe a comparison of the analgesic potency of some prostaglandin synthesis inhibitors, including SC-19220 (see structure above), and morphine using the writhing test. SC-19220 is discussed on Page 133, Lines 10 and 14–16, in Table II (Page 134), and on Page 135, Lines 16–25, and Page 137, Lines 34–38.

A. Bennett et al., "Antagonism of Prostanoid-Induced Contractions of Rat Gastric Fundus Muscle by SC-19220, Sodium Meclofenamate, Indomethacin or Trimethoquinol," *Br. J. Pharmac*, 71, 169–175 (1980), disclose the study of the effects of several compounds, including SC-19220 (see structure above), on contractions of the rat stomach longitudinal muscle to several prostanoids. SC-19220 is discussed on Page 175, Paragraph 1, Page 170, Paragraph 4, in Table 1 and FIG. 2, on Page 172, Paragraph 2, and on Page 174, Paragraphs 1 and 2.

C A Maggi et al., "The Effect of SC-19220, a Prostaglandin Antagonist, on the Micturition Reflex in Rats," *European Journal of Pharmacology*, 152, 273–279 (1988), disclose a study in which SC-19220 (see structure above) is said to have increased the bladder capacity and reduced the voiding efficiency of micturition of urethane-anesthetized rats.

George et al., "Antagonism of Alcohol Hypnosis by Blockade of Prostaglandin Synthesis and Activity: Genotype and Time Course Effects," *Pharmacology Biochemistry & Behavior*, 19, 131–136 (1983), disclose a study of genetic and time-course factors of the effect of the antagonism of alcohol-induced behaviors of mice which have been pretreated with prostaglandin synthetase inhibitors and the effect of SC-19220 (see structure above) on ethanol sleep time.

S Nakajyo et al., "Inhibitory Effect of Bassianolide, A Cyclodepsipeptide, on Drug-Induced Contractions of Isolates Smooth Muscle Preparations," *Japan. J. Pharmacol.*, 32, 55–64 (1982), disclose a study of the effect of bassianolide on the contractile responses induced by various types of neurotransmitters and autacoids. SC-19220 (see structure above) was employed in this study and is discussed on Page 57, Paragraph 1, in FIGS. 2 and 3, in Table 1, and on Page 60, Paragraph 1, Page 62, Paragraph 3, and Page 63, Paragraph 2.

A Gomes et al., "Pharmacodynamics of Venom of the Centipede *Scolopendra subspinipes dehaani*," *Indian Journal of Experimental Biology*, 20, 615–618 (1982), disclose an investigation of the pharmacodynamic actions of the venom of the tropical centipede *S. subspinipes*. SC-19220 (see structure above) was employed in this study and is discussed on Page 615 (abstract), Page 616, Line 30, Page 617, Lines 13–18, in FIGS. 4 and 5, and on Page 618, Lines 23–26.

Each of the documents described hereinabove discloses compounds which are structurally different from the compounds of the present invention. Thus, the compounds of the present invention are structurally distinct from that which has been described in the art.

Compounds of the present invention have been found to exhibit activity as prostaglandin E$_2$ antagonists.

SUMMARY OF THE INVENTION

The present invention provides compounds having a structure of Formula I

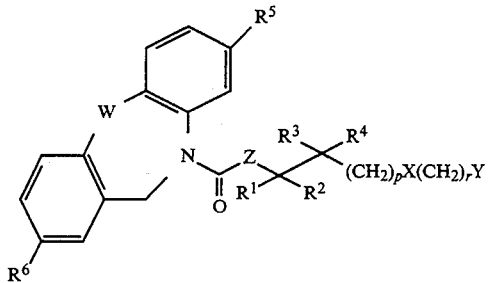

Formula I and the stereoisomers and pharmaceutically acceptable salts thereof, wherein Z represents —$CH_2$—$CH_2$—, —CH=CH— or —C≡C—;

$R^1$, $R^2$, $R^3$ and $R^4$ independently represent hydrogen, lower alkyl, hydroxy, oxytrimethylsilyl or a glycyl ester (glycyloxy) or $R^1$ and $R^2$ together or $R^3$ and $R^4$ together form oxygen;

W represents oxygen, sulfur, sulfoxide, sulfone or $NR^8$ wherein $R^8$ is hydrogen or lower alkyl;

$R^5$ represents hydrogen, halogen, or trifluoromethyl;

$R^6$ represents hydrogen, halogen or $OR^7$ wherein $R^7$ is hydrogen or lower alkyl;

p represents an integer of from 0 to 5;

X represents —$(CH_2)_s$— wherein s is an integer of from 1 to 5, sulfur, sulfoxide, sulfone, oxygen or —NH—;

r represents an integer of from 0 to 5; and

Y represents hydrogen or aryl.

The present invention also provides pharmaceutical compositions which are pharmaceutically acceptable and which comprise a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

DETAILED DESCRIPTION OF THE INVENTION

Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The abbreviation "MPLC" as used herein means Medium Pressure Liquid Chromatography.

The abbreviation "DSC" as used herein means differential scanning calorimetry.

The term "lower alkyl" as used herein means a saturated hydrocarbon radical having from one to six carbon atoms, within which includes from one to three carbon atoms, which can be a straight or branched chain. Representative of such radicals are methyl, ethyl, n-propyl, isopropyl, n-butyl, sec-butyl, isobutyl, tert-butyl and the like.

The term "aryl" as used herein means 5- and 6membered single-ring aromatic radicals which may include from zero to four heteroatoms, within which includes from zero to two heteroatoms. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The abbreviation "$Bu_4NF$" as used herein means tetrabutylammonium fluoride.

The abbreviation "$Bu_3Sn$" as used herein means tributylstannyl.

The abbreviation "$^{13}C$ NMR" as used herein means $^{13}$Carbon Nuclear Magnetic Resonance.

The term "flash chromatography" as used herein is a form of column chromatography, which is known by those of skill in the art, and which is described in J. Org. Chem. 1978, 43,2923.

The term "analgesia" as used herein means the reduction, or absence, of sensibility to pain, designating particularly the relief of pain without loss of consciousness.

The term "animal" as used herein includes mammals and nonmammals, and further includes humans and nonhuman mammals.

The abbreviation "Boc" as used herein means t-butyloxycarbonyl.

The abbreviation "DCC" as used herein means dicyclohexylcarbodiimide.

The abbreviation "DMSO" as used herein means dimethylsulfoxide.

The abbreviation "OTMS" and the term "oxytrimethylsilyl" as used herein mean

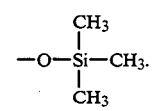

The abbreviation "THF" as used herein means tetrahydrofuran.

The abbreviation "DMAP" as used herein means dimethylaminopyridine.

The abbreviation "DSC" as used herein means Differential Scanning Calorimetry.

The term "composition" as used herein means a product which results from the combining of more than one ingredient.

The phrase "$ED_{50}$ dose" as used herein means that dose of a compound or drug which produced a defined biological effect, such as producing analgesia, in 50% of the animals to which the compound or drug was administered.

The abbreviation "EtoAc" as used herein means ethyl acetate.

The abbreviation "Et" as used herein means ethyl (—$CH_2CH_3$).

The abbreviation "$Et_3N$" as used herein means triethylamine.

The abbreviation "Gly" as used herein means the amino acid glycine.

The term "heteroatom" as used herein means an atom of any element other than carbon or hydrogen.

The phrase "a glycyl ester" as used herein means

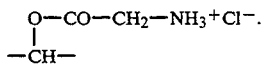

The term "halo" or "halogen" as used herein means chlorine (Cl), bromine (Br), fluorine (F) and/or iodine (I).

The term "hydroxy" as used herein means the group —OH.

The abbreviation "¹H NMR" as used herein means Proton Nuclear Magnetic Resonance.

The term "intragastrically" and/or the abbreviation "i.g." as used herein mean that a compound or drug was administered into the stomach.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The abbrevitation "Me" as used herein means methyl (—CH₃).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmirate, stearate, laurate, benzoate, lactate, phosphate, tosylate, citrate, maleate, fumarate, succinate, tartrate, napsylate, clavulanate and the like salts and alkali metal salts such as sodium and potassium salts and alkaline earth salts, such as calcium and magnesium.

The term "phenyl" as used herein means the group C₆H₅—, derived from benzene.

The abbreviation "s.c." as used herein means that a compound or drug was administered subcutaneously.

The phrase, "side chain" as used herein, means functionalization of the N-10 position of the molecule.

The term "sulfoxide" as used herein means

The term "sulfone" as used herein means

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The abbreviation "TLC" as used herein means Thin Layer Chromatography.

The term "trifluoromethyl" as used herein means a —CF₃ group.

(2) Description of Invention

In one aspect, the present invention provides compounds comprising a structure of Formula I, as described above, and pharmaceutically-acceptable salts, esters and amides thereof.

The compounds of the present invention comprise a class of substituted dibenzoxazepine compounds in which the 2-, 5- and/or 8-position and/or the side chain is substituted. Compounds within the present invention have been shown to exhibit activity as prostaglandin E₂ antagonists.

Specific compounds within the scope of the invention include, but are not limited to, the compounds discussed in the examples presented below, as well as their pharmaceutically-acceptable salts, esters, and amides.

Certain compounds of this invention may exist in geometric or stereoisomeric forms. The present invention contemplates all such compounds, including cis- and trans- geometric isomers, R- and S-enanticmers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Certain compounds of the present invention may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmirate, stearate, laurate, benzoate, lactate, phosphate, tosylate, titrate, maleate, fumarate, succinate, tartrate, napthylate, mesylate, glucoheptonate, lactobionate, and laurylsulphonate salts and the like. (See, for example, S. M. Berge et al., "Pharmaceutical Salts," *J. Pharm. Sci.,* 66: 1-19 (1977).)

In other cases, the compounds of the invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Bergs et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal, and methods for treating central nervous system disorders, including convulsions and ischemia, and asthma, enuresis, arrhythmia, diarrhea, dysmenorrhea and osteoporosis in an animal, comprising administering a therapeutically-effective amount of a compound of Formula I, as described hereinabove, to the animal.

The most preferred embodiment of the present invention is the compound described in Example 17 below.

(3) Utility

Compounds of the present invention exhibit activity as prostaglandin $E_2$ antagonists (prostaglandin antagonists of the $E_2$ series).

Compounds within the present invention, and the pharmaceutical compositions comprising one or more of these compounds, are useful as analgesic agents for the elimination or amelioration of pain in animals.

In addition to treating pain, these compounds and compositions would be useful in treating convulsions, ischemia and other central nervous system disorders, as well as osteoporosis, dysmenorrhea, asthma, enuresis, arrhythmia, urinary incontinence, gastric hypermotility, irritable bowel syndrome and diarrhea, by virtue of their activity as prostaglandin $E_2$ antagonists.

(4) Methods of Preparation

In general, the compounds of the present invention may be prepared by the methods illustrated in the following general reaction schemes, or by modifications thereof, using readily-available starting materials, reagents and conventional synthesis procedures. Unless otherwise specified, the various substituents of the compounds and materials present in the general reaction schemes are defined in the same manner as they are defined above in Formula I.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers. The compounds of this invention may be prepared by the methods illustrated in the following reaction schemes.

As shown in General Reaction Scheme No. 1, the heterocycle can be reacted with phosgene to form the carbamoyl chloride. This material can then be reacted with a vinyl stannane in the presence of a palladium catalyst to form the $\alpha,\beta$-unsaturated amides, or reacted with an alkyne in the presence of a palladium catalyst-/copper iodide to form the amide. The silyl protecting groups can then be removed by tetrabutyl ammonium fluoride.

As shown in General Reaction Scheme No. 2, the heterocycle can be reacted with an appropriate acid chloride to form the amide.

As shown in General Reaction Scheme No. 3, the resulting alcohols in General Reaction Scheme-No. 1 can be oxidized to form the corresponding ketones. Alternatively the alcohol can be esterified with a N-protected amino acid followed by removal of the protecting group from the amine.

As shown in General Reaction Sceme No. 4, the heterocycle can be reacted with succinic anhydride/DMAP, followed by the formation of the N,O-dimethyl hydroxamide. This material can then be reacted with alkynyl anion to form the ketone. The alkyne can then be reduced with Hydrogen/Raney-Nickel.

General Reaction Scheme No. 1
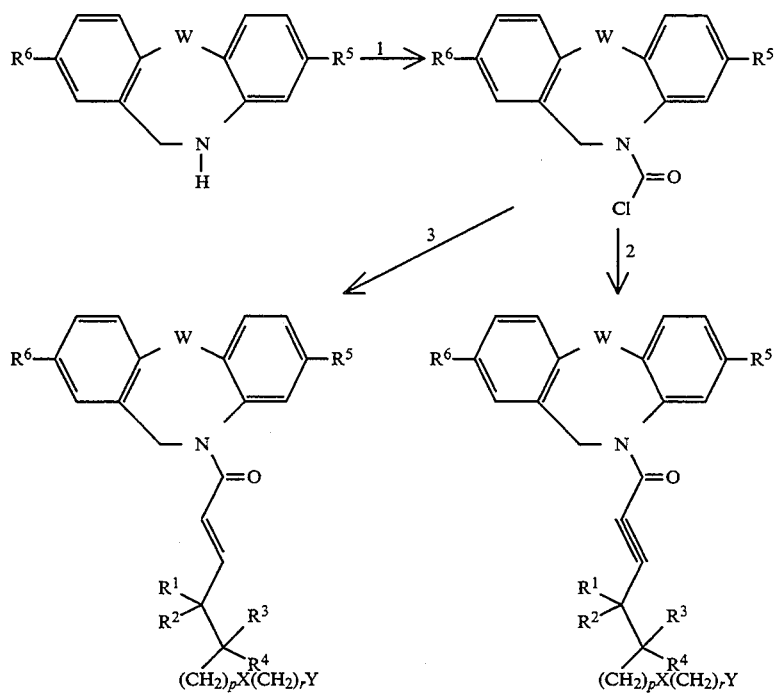
1) COCl$_2$/Et$_3$N
2) i) Alkyne/Pd(II) catalyst/CuI
   ii) Bu$_4$NF
3) i) Vinyl Stannane/Pd(II) catalyst
   ii) Bu$_4$NF
General Reaction Scheme No. 2
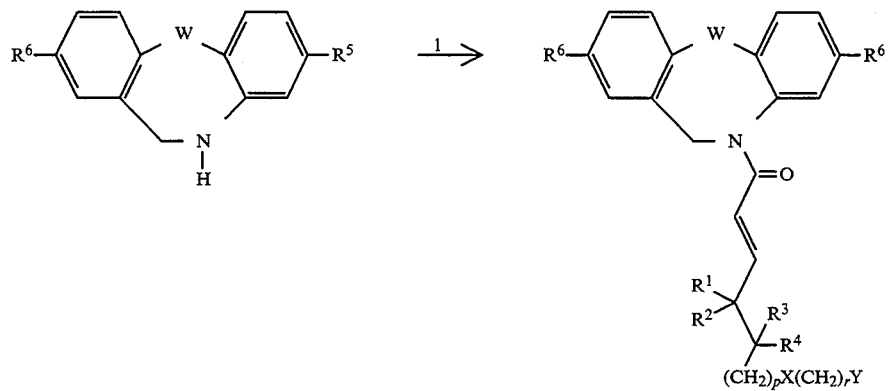
1) acid chloride/Et$_3$N
General Reaction Scheme No. 3
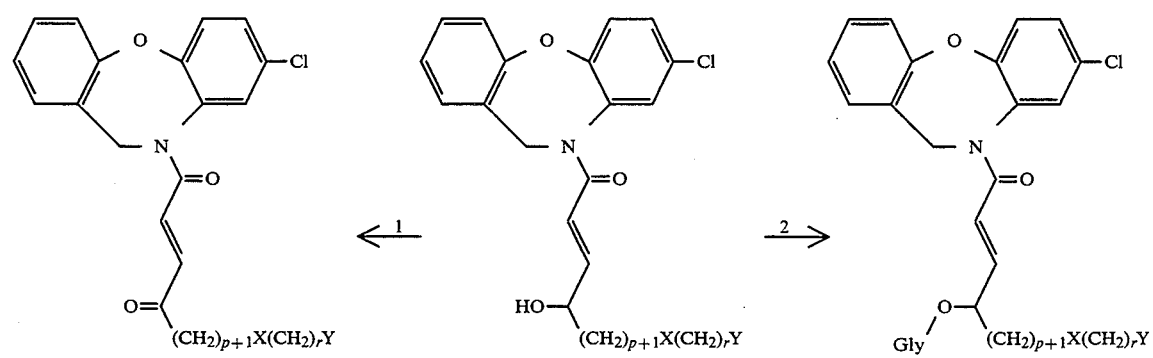
1) (COCl)$_2$/DMSO
2) i) N—Boc Gly/DCC  ii) HCl General Reaction for Scheme No. 4

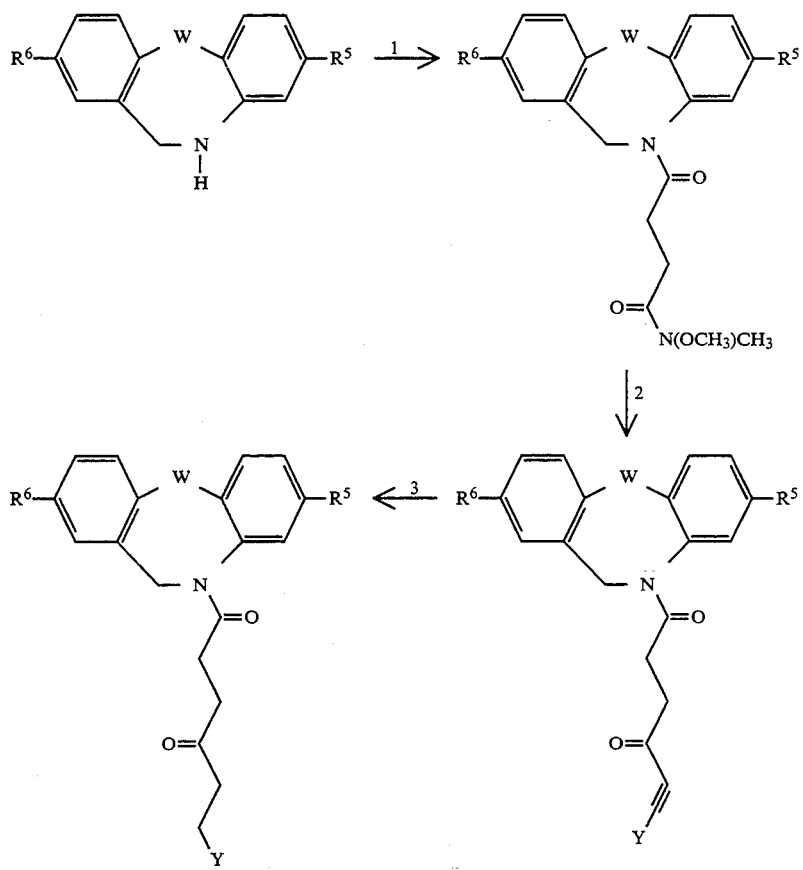

1) i) succinic anhydride/DMAP
2) isobutylchloroformate/N,O-dimethyl hydroxylamine
3) H₂/Raney-Nickel The conditions for carrying out the individual steps in each of the general reaction schemes presented above are conventional, well-known, and capable of wide variation.

Other methods known in the art can also be used to synthesize the compounds of the present invention.

EXAMPLES

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate.

Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

All equipment employed in the examples is commercially available. Unless otherwise indicated, all starting materials employed in the examples are commercially available. Sources for these materials include Sigma Chemical Co. (St. Louis, Mo.), Aldrich Chemical Co. (Milwaukee, Wis.), Lancaster Synthesis (Windham, N.H.), Fisher Scientific (Pittsburgh, Penna.), Boshringer Mannheim Biochemicals (Indianapolis, Ind.), Fluka Chemical Corp. (Ronkonkoma, N.Y.) and Chemical Dynamics Corp. (South Plainfield, N.J.). Most of the starting materials were obtained from Aldrich Chemical Co. (Milwaukee, Wis.).

All patents and publications referred to in the examples, and throughout the specification, are hereby incorporated herein by reference, without admission that such is prior art.

EXAMPLE 1

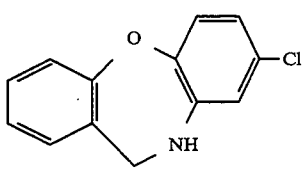

8-chloro-10,11-dihydrodibenz[b,f][1,4]oxazepine (1)

The synthesis of 1 is described in U.S. Pat. No. 3,534,019, which is incorporated herein by reference.

Briefly, 200 parts of 2,5-dichloro-nitrobenzene were heated to 160° C. and stirred, and 160 parts of the potassium salt of salicylaldehyde was added over a period of 30 minutes. After the addition was complete, an exothermic reaction took place, and the temperature rose to about 195° C. Heating was discontinued until the reaction subsided, and the mixture was heated for 1 hour. at 150° C. The mixture was cooled, ice and water were added, and it was extracted with ether. The ether layer was filtered to remove insoluble material, and the resultant solution was dried over sodium sulfate. The ether solvent was evaporated, and the residual oil was recrystallized from a mixture of hexane and benzene to give 2-(2-nitro-4-chloro-phenoxy)benzaldehyde melting at about 100°–101° C.

A solution of 55 parts of the ether obtained in the preceding paragraph in 800 parts of ethanol was hydrogenated over Raney nickel catalyst at room temperature and atmospheric pressure. When hydrogen uptake ceased, the catalyst was removed by filtration, and the ethanol solvent was evaporated. The residue was dissolved in 500 parts by volume of hexane, filtered, and cooled. There was obtained yellowish-white crystals which were separated by filtration to give 8-chloro-10,11-dihydrodibenz-[b,f][1,4]oxazepine melting at about 94°–95° C.

EXAMPLE 2

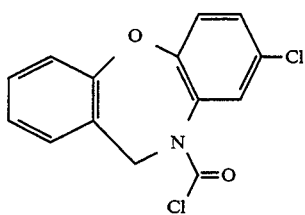

8-chlorodibenz[b,f][1,4]oxazepine-10(11H)-carbonl chloride (2)

The synthesis of 2 is described in U.S. Pat. No. 3,534,019, which is incorporated herein by reference.

Briefly, 13 parts of phosgene in 45 parts of toluene was stirred for 2 hours at 5°–10° C., and then 70 parts of ether was added. This was followed by the addition of a solution of 18.9 parts of 8-chloro-10,11-dihydrodibenz[b,f][1,4]oxazepine and 7.2 parts of triethylamine in 140 parts of ether. After the addition was complete, the mixture was stirred for 2 hours, and then was filtered. The solvent was then evaporated from the flitrate. The resulting residue was then dissolved in 200 parts by volume of hot hexane, and this mixture was then filtered and cooled.

EXAMPLE 3

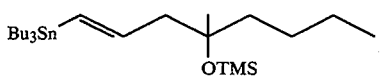

[[1-methyl-1-[3-(tributylstannyl)-2E-propenyl]pentyl]oxy]trimethylsilane (3)

The synthesis of 3 is described in P.W. Collins et. al. J. Med. Chem. 26, 786 (1983), which is incorporated herein by reference.

Briefly, a mixture of 2.12 g (10 mmol) of [[1-methyl-1-[2-propynyl]pentyl]oxy]trimethylsilane and 2.91 g (10 mmol) of tri-n-butyltin hydride contained in a Pyrex round-bottomed flask was irradiated under argon with a General Electric sunlamp for 2 hours at room temperature (a circulating water bath is required) and then at about 55° C. (heat generated by lamp) for 2 hours. The resulting product was used directly in Example 4 below.

EXAMPLE 4

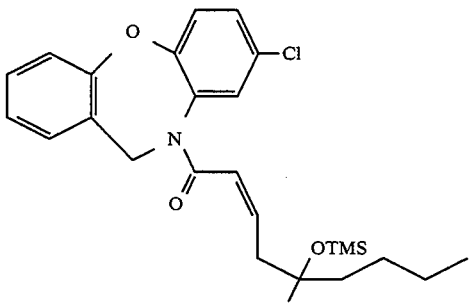

8-chloro-10,11-dihydro-10-[5-methyl-1-oxo-5-[(trimethylsilyl)oxy]-2Z-nonenyl]-dibenz[b,f][1,4]oxazepine (4)

To a room temperature solution of 2 (1.0 g, 3.4 mmol) and 3 (1.88 g 3.7 mmol) in dry THF (50 mL) under $N_2$ was added bis(triphenylphosphine)palladium chloride (400 mg, 0.57 mmol). The resulting solution was refluxed for 20 hours. The reaction mixture was poured onto ether and extracted with brine, dried over $MgSO_4$ and reduced to yield a brown oil. The product was chromatographed MPLC (silica gel, 1:9 ether:hexane) to yield 4 as a yellow oil (110 mg). Analysis calculated for $C_{26}H_{34}ClNO_3Si$: C: 66.15; H: 7.26; N: 2.97. Found C: 66.59; H: 7.14; N: 2.69.

EXAMPLE 5

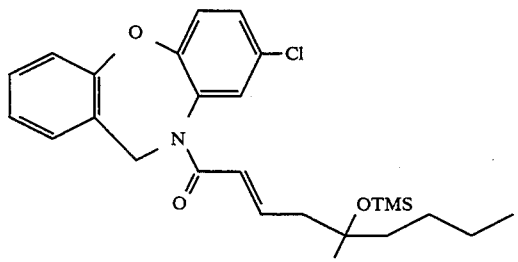

8-chloro-10,11-dihydro-10-[5-methyl-1-oxo-5-[(trimethylsilyl)oxy]-2E-nonenyl]-dibenz[b,f][1,4]oxazepine (5)

To a room temperature solution of 2 (10.0 g, 34 mmol) and vinyl stannane 3 (18.8 g, 37 mmol) in dry THF (500 mL) under $N_2$ was added bis(triphenylphosphine)palladium chloride (2.5 g, 3.5 mmol). The resulting solution was stirred at room temperature for 1 hour, then refluxed for 48 hours. The reaction mixture was poured onto ether and extracted with brine, dried over $MgSO_4$ and reduced to yield a brown oil. The product was chromatographed MPLC (silica gel, 1:9 ether:hexane) to yield 5 as a yellow oil (630 mg). Analysis calculated for $C_{26}H_{34}ClNO_3Si$: C: 66.15; H: 7.26; N: 2.97. Found C: 66.59; H: 7.14; N: 2.69. A large amount of the decarbonylation product 1 was observed.

EXAMPLE 6

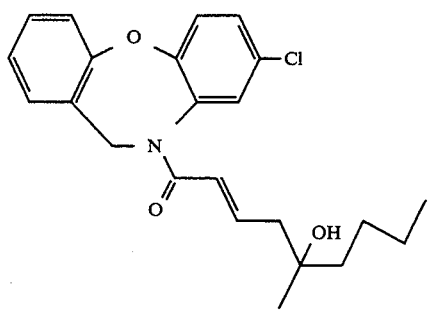

8-chloro-10,11-dihydro-10-(5-hydroxy-5-methyl-1-oxo-2E-nonenyl)dibenz[b,f][1,4]oxazepine (6)

To a stirring solution of 5 (2.0 g), was added tetrabutyl ammonium fluoride (22 mL, 22 mmol in THF). The crude product was used due to the difficulty of separating compounds 1 and 5. The reaction mixture was stirred for 45 minutes at room temperature. The solvent was removed under reduced pressure and the residue was taken up in CHCl₃, extracted with brine and dried (K₂CO₃). The product was purified by MPLC (silica gel, 3:7 EtOAc:hexane) to yield 6 as a yellow oil (50 mg). Analysis calculated for $C_{23}H_{26}ClNO_3$: C: 69.08; H: 6.55; N: 3.50. Found C: 69.33; H: 6.64; N: 3.45.

EXAMPLE 7

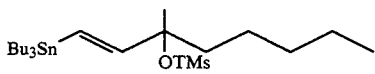

[[1-methyl-1-[2-(tributylstannyl)-Z-ethenyl]hexyl]oxy]-trimethylsilane (7)

The compound 7 was prepared according to the procedure for the synthesis of 3. The 3-methyl-3-trimethylsilyloxy 1-octyne (48 retool) was treated with tributyl tinhydride to yield 7 (66 %).

EXAMPLE 8

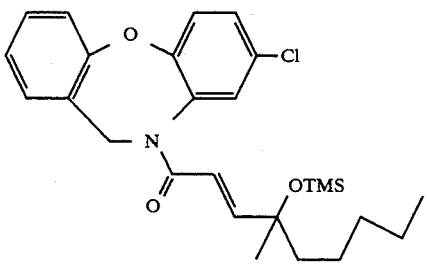

8-chloro-10,11-dihydro-10-[4-methyl-1-oxo-4-[(trimethylsilyl)oxy]-2E-nonenyl]dibenz-[b,f][1,4]oxazepine (8)

A solution of 2 (1.0 g, 3.4 mmol), 7 (3.34 g, 6.8 mmol) and trans-benzyl(chloro)bis(triphenylphosphine) palladium (II) (100 mg, 0.13 mmol) in dry THF (50 mL) was refluxed lander an argon atmosphere for 16 hours. The reaction mixture was poured onto ether and extracted with brine. The material was then passed through a plug of silica gel which was washed with ether. The resulting oil was purified by MPLC (silica gel, 3:7 ether:hexane) to yield 1.47 g of an oil. TLC analysis showed the presence of the desired product and 1. The product was rechromatagraphed to yield 680 mg of pure product 8 as an oil, and 720 mg of the mixture (23% 1 by ¹H NMR). Analysis calculated for $C_{26}H_{34}ClNO_3 5Si.0.25 H_2O$: C: 65.52; H: 6.55; N: 3.50. Found: C: 65.43; H: 7.22; N: 3.49.

EXAMPLE 9

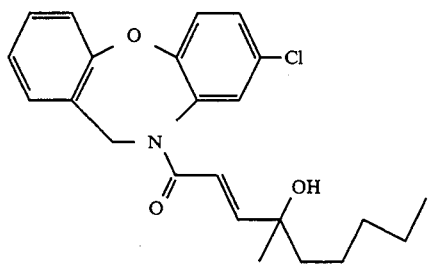

8-chloro-10,11-dihydro-10-(4-hydroxy-4-methyl-1-oxo-2E-nonenyl)dibenz[b,f][1,4]oxazepine (9)

To a stirring solution of 8 (400 mg, 0.84 mmol) in THF (45 mL) under a N₂ atmosphere at room temperature was added tetrabutylammonium fluoride in THF (5 mL, 5 mmol). The reaction solution was stirred for 2 hours, then the solvent was removed and the residue was taken up in CHCl₃, extracted with brine, and dried over Na₂SO₄ to yield 3.5 g of an oil. The material was chromatographed (MPLC, 4:1 EtOAc:hexane) to yield 310 mg of 9 as an oil. Analysis calculated for $C_{23}H_{26}ClNO_3.1 H_2O$; C: 66.10; H: 6.75; N: 3.35. Found: C: 66.20; H: 7.15; N: 2.89.

EXAMPLE 10

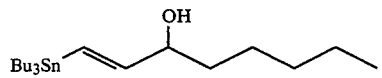

1-(tributylstannyl)-1E-octen-3-ol(10)

The compound 10 was prepared according to the procedure for the synthesis of 3. The 1-octyn-3-ol (23 mmol) was treated with tributyl tinhydride to yield 10 (95%).

EXAMPLE 11

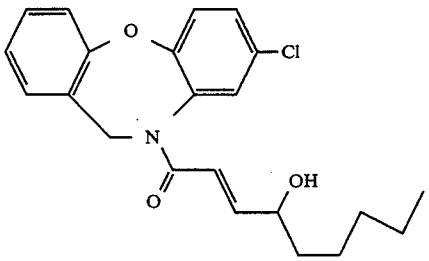

8-chloro-10,11-dihydro-10-(4-hydroxy-1-oxo-2E-nonenyl)dibenz[b,f]1,4]oxazepine (11)

A solution of 2 (2.94 g, 10 mmol), 10 (9.0 g, 20 mmol) and trans-benzyl(chloro)bis(triphenylphosphine) palladium (II) (200 mg, 0.26 mmol) in dry THF (150 mL) was refluxed under an argon atmosphere for 16 hours. The solvent was removed and the residue was purified by flash column chromatography on silica gel (85:15, hexane:EtOAc) to yield an oil (3.31 g). The product was crystallized from hexane to yield 11 (2.3 g). DSC 78.7° C. Analysis calculated for $C_{22}H_{24}ClNO_3$. 0.25 $H_2O$: C: 66.15; H: 7.26; N: 2.97. Found C: 66.59; H: 7.14; N: 2.69.

EXAMPLE 12

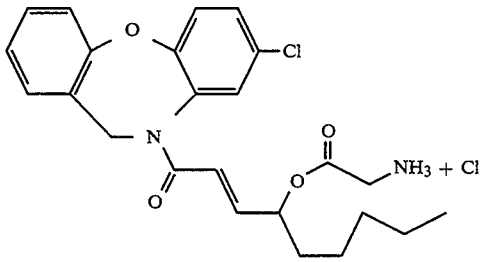

glycine, 1-[3-(8-chloro-10,11-dihydrodibenz-[b,f][1,4]oxazepin-10-yl)-3-oxo-1E-propenyl]-hexyl ester, monohydrochloride (12)

To a solution of 11 (800 mg, 2.1 mmol) and DMAP in $CH_2Cl_2$ was added a solution of the anhydride of N-Boc glycine ( 2.5 mmol) in $CH_2Cl_2$ ( 10 mL). The reaction solution was stirred at room temperature for 16 hours. The solvent was removed and the residue was flash chromatographed on silica gel (85:15 hexane:EtOAc) to yield 310 mg of an oil. To a stirring solution of the oil in $CH_2Cl_2$ (50 mL) was added a solution of HCl in dioxane (6.95M). The resulting solution was stirred at room temperature for 1 hour followed by the removal of solvent. The residue was dissolved in water and lyophilized to yield 12 (335 mg). DSC 215.6° C. Analysis calculated for $C_{24}H_{27}ClN_2O_4$. HCl. 0.8 $H_2O$: C: 58.37; H: 6.04; N: 5.67; Cl:14.36. Found C: 58.56; H: 6.07; N: 5.17; Cl:13.9.

EXAMPLE 13

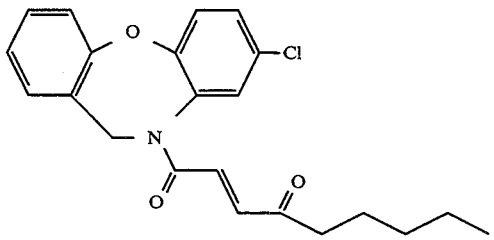

8-chloro-10,11-dihydro-10-(1,4-dioxo-2E-nonenyl)-dibenz[b,f][1,4]oxazepin (13)

To a cooled solution of oxalylchloride (0.25 mL, 2.75 mmol) in methylene chloride at −70° C. was added DMSO. After 2 minutes, a solution of the alcohol 11 (700 mg, 1.8 mmol) in methylene chloride (3 mL) was added. The reaction solution was stirred at −20° C. for 1 hour followed by the addition of triethylamine (1.75 mL, 11 mmol). After 5 minutes the reaction mixture was poured onto methylene chloride and extracted with $NaHCO_3$, brine, dried over $Na_2SO_4$ and evaporated to yield an oil that was purified by MPLC (silica gel; 85:15, Hexane:EtOAc). The resulting oil was crystallized from hexane to yield 13 (92 mg). DSC 88.02° C. Analysis calculated for $C_{22}H_{22}ClNO_3$: C: 68.83; H: 5.78; N: 3.65. Found C: 68.61; H: 5.71; N: 3.62.

EXAMPLE 14

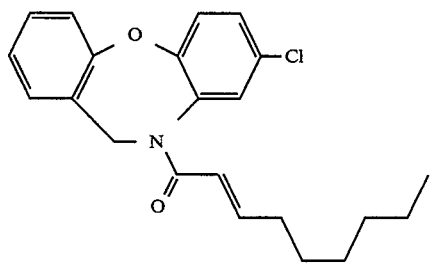

8-chloro-10,11-dihydro-10-(1-oxo-2E-nonenyl)-dibenz[b,f][1,4]oxazepine (14 )

To a stirring solution of 1 (2.1 g) in methylene chloride (50 mL) and triethylamine (1 mL) was added nonenoic acid chloride (3.0 mL). The resulting solution was stirred for 36 hours at room temperature. The reaction mixture was then poured onto $CHCl_3$ (300 mL) and extracted with HCl (1M), $NaHCO_3$ and brine, dried ($Na_2SO_4$) and evaporated to yield 4.4 g of an orange solid. The material was purified by chromatography on silica gel (85:15 hexane:EtOAc) to yield 14 (2.65 g) as an oil. Analysis calculated for $C_{22}H_{24}ClNO_2$: C: 71.44; H: 6.54; N: 3.79. Found C: 71.23; H: 6.55; N: 3.73.

EXAMPLE 15

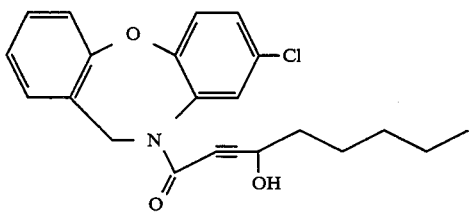

8-chloro-10,11-dihydro-10-(4-hydroxy-1-oxo-2-nonynyl)dibenz[b,f][1,4]oxazepine (15)

A solution of 2 (2.0 g, 6.8 mmol), octyne-3-ol (0.87 g, 6.8 mmol), trans-benzyl(chloro)bis (triphenylphosphine)-palladium (II) (100 mg, 0.13 mmol), and copper iodide (100 mg) in triethylamine (40 mL) was refluxed under an argon solution for 16 hours. The solvent was removed and the residue was taken up in EtOAc and extracted with HCl (1M) and brine, dried ($Na_2SO_4$) and evaporated to yield a brown oil. The product was chromatographed on silica gel (85:15 hexane:EtOAc) to yield 15 as an oil (390 mg). Analysis calculated for $C_{22}H_{22}ClNO_3$. 0.5 $H_2O$: C: 67.25; H: 5.90; N: 3.57. Found C: 67.32; H; 5.87; N: 3.35.

EXAMPLE 16

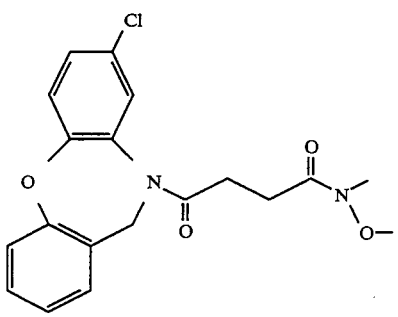

8-chloro-N-methoxy-N-methyl-γ-oxodibenz[b,f]-
[1,4]oxazepine-10(11H)-butanamide (16)

A mixture of 8-chlorodibenzoxazepine (5 g), succinic anhydride (5 g), 4-dimethylaminopyridine (4 g) and 1,2-dichloroethane (50 mL) was heated to reflux for 16 hours. The mixture was cooled to room temperature and shaken successively with 0.7 N HCl, water, dried over MgSO4 and concentrated. The residue was chromatographed over silica gel using a mixture of 1/1 ethyl acetate/hexane as eluant. Appropriate fractions were pooled and concentrated in vacuo to leave 5.3 g of a thick gum [$^{13}$C NMR (CDCl3) δ 28.33, 28.69, 48.07]. To a stirred solution of this material (4.9 g) in tetrahydrofuran (50 mL) at 0° C. was added in succession 4-methylmorpholine (1.63 mL) and isobutyl chloroformate (1.92 mL). After 30 minutes, 4-methylmorpholine (1.63 mL) and N,O-dimethylhydroxylamine hydrochloride (1.45 g) were added. The mixture was allowed to warm to room temperature over 2 hours. The mixture was concentrated in vacuo. The residue was extracted with ethyl acetate and water. The organic phase was washed sequentially with diluted HCl and water, dried over MgSO4 and concentrated in vacuo. The residue was chromatographed over silica gel using 3/5 ethyl acetate/hexane as eluant. Appropriate fractions were pooled and concentrated to give 3.4 g of 16 as a thick gum [$^{13}$C NMR (CDCl3) δ 6 26.96, 28.23, 32.04, 32.07, 48.16, 60.98].

EXAMPLE 17

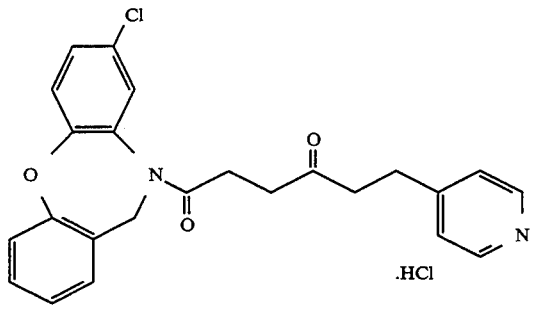

8-chloro-10-[1,4-dioxo-6-(4-pyridinyl)hexyl]-10,11-dihydrodibenz[b,f][1,4]-oxazepine, monohydrochloride (17)

To a stirred solution of 4-ethynylpyridine (1 g) in THF (25 mL) at −78° C. was added a hexane solution of n-butyl lithium (1.6 M, 6.0 mL). After 20 minutes, a solution of 16 (3.34 g) in THF (10 mL) was added. After 30 minutes, the temperature was raised to 0° C. over 1 hour. The reaction mixture was quenched with saturated aqueous NH4Cl and extracted with ethyl acetate. The organic phase was dried over MgSO4 and concentrated in vacuo. The residue was chromatographed over silica gel using a mixture of 3/5 ethyl acetate/hexane as eluant. Appropriate fractions were pooled and concentrated to give 1.79 g of a thick gum [$^{13}$C NMR (CDCl3) δ 8 27.29, 39.50, 47.71]. A solution of this material (0.694 g) in ethyl acetate (30 mL) was shaken with Raney-Nickel (1 g) in a parr hydrogenation apparatus at room temperature under 5 psi hydrogen atmosphere for 30 minutes. The mixture was filtered and the filtrate was concentrated in vacuo. The residue was chromatographed over silica gel using ethyl acetate as eluant. Appropriate fractions were pooled and concentrated to give 0.3 g of the free base of 17 as a thick gum, A solution of this material in CH2Cl2 (3 mL) and 7 N HCl in dioxane (3 mL) was concentrated in vacuo. The residue was taken up in water (15 mL) and lyophilized to give 17 as a white solid. [$^{13}$C NMR (DMSO-d6) δ 27.6, 28.5, 36.5, 40.5, 47.3]. Analysis Calculated for C24H21ClN2O3. HCl. H2O: C: 60.64; H: 5.09; N: 5.89; Cl: 14.92. Found: C: 60.46; H: 5.19; N: 5.36; Cl: 13.61.

The biological activities of the compounds of this invention were determined by the following test procedures.

DESCRIPTION OF ASSAYS (a) Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., Arch. int. Pharmacodyn, 267, 131–140 (1984); C. Vander Wende et al., Fed. Proc., 15, 494 (1956); Koster et al., Fed. Proc., 18, 412 (1959); and Witken et al., J. Pharmacol. exp. Ther., 133, 400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table I below.

Charles River male albino mice, weighing 20 to 30 grams were used in this assay.

Thirty minutes after subcutaneous or intragastric administration to ten mice of 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following tenminute period was counted.

A test compound was considered to have produced analgesia in a mouse if, in accordance with the conditions set forth above, and under the test criteria employed for this assay, after the administration of 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," *Advances in Biochemical Psychopharmacology*, 8, 191 (1974).

The standard initial screening dose of a test compound employed in this assay was 30 mpk per gram of body weight for both routes of administration. If this initial screening dose of the test compound produced analgesia in seven of ten mice, then the effect of additional doses of the test compound on the writhing response was evaluated, and then the $ED_{50}$ dose was generally calculated. (The slopes of the dose-response curves for all test compounds analyzed were compared as described by Taltarida and Murray, *Manual of Pharmacologic Calculations*, Page 11 (Springer Verlag, New York, 1981)).

The results for the particular compounds of the present invention analyzed in this assay, and discussed in the examples identified below which correspond thereto, are presented in Table I hereinbelow under the heading "PBQ WRITHING ASSAY". The fractions indicate the number of mice out of 9 or 10 in which the initial screening dose of a test compound produced analgesia. The numbers which are not fractions represent $ED_{50}$ doses.

As Table I shows, the rank order of potency of the more potent compounds of the present invention tested in the Writhing Assay was (referring to the particular example which describes the preparation of the compound): Example 17 > Example 9 > Example 4 > Example 8 > Example 5 > Example 12. Thus, the compound of Example 17 was determined to be the most potent compound of the invention tested in this assay, and is the most preferred compound of the present invention.

(b) Prostaglandin (PGE) Antagonism Assay

In order to determine the effectiveness of several of the compounds of the present invention ("test compounds") as prostaglandin $E_2$ antagonists, a prostaglandin antagonism assay was conducted, as described below, to determine the ability of these compounds to inhibit prostaglandin $E_2$-induced contractions of segments of guinea pig ileum. If a test compound inhibits prostaglandin $E_2$-induced contractions, it suggests that the compound functionally antagonizes prostaglandin $E_2$.

Male albino guinea pigs weighing 200 to 500 grams were sacrificed by cervical dislocation.

The ileums were then quickly removed from the guinea pigs and placed in a modified Tyrode solution, a solution which is known to those of skill in the art, containing one-half of the usual amount of magnesium ions.

Segments of ileum about 2 cm long were then cut and mounted in a 10-mL tissue bath containing the modified Tyrode solution. The solution was maintained at 37° C. and aerated with a gaseous mixture of 95% oxygen and 5% carbon dioxide.

Submaximal contractions of the ileum segments were then generated by injecting prostaglandin $E_2$ into the bath, and detected isotonically. Data for a control prostaglandin $E_2$ dose response curve plotting concentration of prostaglandin $E_2$ versus number of contractions generated was then obtained by experimentally adjusting the dose of the prostaglandin $E_2$ being injected into the tissue bath, in a manner known by those of skill in the art.

Solutions or suspensions containing an initial amount of a test compound in modified Tyrode solution ("test solutions/suspensions") were then separately substituted for the tissue bath. Each test solution/suspension was then kept in constant contact with the ileum tissue, except for brief periods to drain the bath in preparation for rinsing with fresh test solution/suspension. Different doses of prostaglandin $E_2$ were again injected into the test solutions/suspensions.

A second prostaglandin $E_2$ dose response curve was then generated for $PGE_2$ in the presence of a test compound.

A dose ratio of $EC_{50}$ doses (that dose of a compound or drug which is necessary to elicit a 50% maximal biological response and, thus, which is necessary to elicit a 50% reduction in the contractions of %he guinea pig ileum segments in this assay) was then calculated from the results of each test in a manner known by those of skill in the art. A concentration of test compound was determined to be "active" if it produced a dose ratio significantly greater than that obtained in a series of blank treatments. Duplicate tests were conducted on each concentration of test compound.

If the initial concentration of a test compound was determined to be "active," then varying concentrations of the test compound were then assayed.

The $pA_2$ value (a statistical constant which is a common measure of expressing the potency of a particular drug as a competitive antagonist) was then calculated for each test compound by schild plot calculations, as described by H. O. Schild, "pA A New, Scale for the Measurement of Drug Antagonism, " *Br. J. Pharmacol*, 2, 189 (1947), according to the following mathematical formula:

$$pA_2 = -\log[\text{Test Compound}]$$

to quantitate the effectiveness of the test compounds as prostaglandin $E_2$ antagonists. The higher the value calculated for $pA_2$, the more potent a particular compound is as a prostaglandin $E_2$ antagonist.

The results of this prostaglandin antagonism assay are also presented in Table I below. The compounds of the present invention which were tested in this assay, and for which results are presented in Table I, correspond to the particular examples specified in Table I.

The results in Table I show that each of the compounds of the present invention tested in this assay exhibited activity as a prostaglandin $E_2$ antagonist.

TABLE I

| | Data Generated from the Assays | | |
|---|---|---|---|
| | PBQ WRITHING ASSAY ($ED_{50}$ (mpk) or No. Out of 10) | | PGE ANTAGONISM IN GUINEA PIG ILEUM |
| EXAMPLE NUMBER | I.G. | S.C. | ($pA_2$) |
| 6 | 4/10 | 4/10 | 6.78 |
| 9 | 5/10 | 9/10 | 6.21 |
| 11 | 2/10 | 3/10 | 6.67 |
| 4 | 5/10 | 8/10 | Not Yet Tested |
| 5 | 3/10 | 6/10 | Not Yet Tested |

TABLE I-continued

| | Data Generated from the Assays | | |
|---|---|---|---|
| | PBO WRITHING ASSAY ($ED_{50}$ (mpk) or No. Out of 10) | | PGE ANTAGONISM IN GUINEA PIG ILEUM |
| EXAMPLE NUMBER | I.G. | S.C. | ($pA_2$) |
| 8 | 6/10 | 4/10 | Not Yet Tested |
| 12 | 5/9 | 3/10 | Not Yet Tested |
| 14 | 1/10 | 1/10 | Not Yet Tested |
| 15 | 1/10 | 3/10 | Not Yet Tested |
| 13 | 1/10 | 2/9 | Not Yet Tested |
| 17 | 5.4 | Not Yet Tested | 6.99 |

DOSAGE AND MODE OF ADMINISTRATION

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a particular patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the present invention will be that amount of the compound which is the lowest dose effective to produce a therapeutic effect. Such an effective dose will generally depend upon the factors described above. Generally, dosage levels in the range of from about 0.001 mg to about 10 g, more preferably from about i mg to about 1000 mg, of active compound (a compound of Formula I) per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alphatocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred per cent, this amount will range from about I per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonits clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile, injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically-acceptable emulsions, microemulsions, solutions, suspensions, syrups and elixirs. In addition to the active ingredient (compound of Formula I), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving, dispersing or otherwise incorporating a compound of the present invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable dosage forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose seaILed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention.

What is claimed is:

1. A compound of the formula

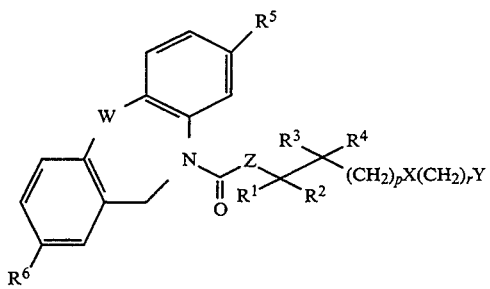

and pharmaceutically acceptable salts thereof, wherein
Z represents —CH$_2$—CH$_2$—, —CH=CH— or C≡C—;

R$^1$, R$^2$, R$^3$ and R$^4$ independently represent hydrogen, a saturated hydrocarbon radical having from one to six carbon atoms which can be a straight or branched chain, hydroxy, oxytrimethylsilyl or glycyloxy or R$^1$ and R$^2$ together or R$^3$ and R$^4$ together form oxygen;

W represents oxygen,

R$^5$ represents hydrogen, halogen, or trifluoromethyl,

R$^6$ represents hydrogen, halogen or OR$^7$ wherein R$^7$ is hydrogen or a saturated hydrocarbon radical having from one to six carbon atoms which can be a straight or branched chain;

p represents an integer of from 0 to 5;

X represents —(CH$_2$)$_s$— wherein s is an integer of from 1 to 5, sulfur, sulfoxide, sulfone, oxygen or —NH—;

Y represents hydrogen or a 5- or 6-membered single ring aromatic radical which may include from zero to four heteroatoms selected from OS and N;

n represents an integer of 0 to 5.

2. A compound of claim 1 wherein
Z represents —CH=CH— or —C≡C—;
R$^1$ represents hydrogen, methyl or hydroxy;
R$^2$ represents hydrogen or oxytrimethylsilyl;
or R$^1$ and R$^2$ together represent oxygen;
R$^3$ represents hydrogen or methyl;
R$^4$ represents hydrogen, hydroxy, oxytrimethylsilyl or glycyloxy
W represents oxygen;
R$^5$ represents halogen;
R$^6$ represents hydrogen;
p represents 1;
X represents —(CH$_2$)$_s$— wherein s is 1;
r represents 1 or 2; and
Y represents hydrogen.

3. A compound of claim 2 wherein
Z represents —CH=CH—;
R$^1$, R$^2$ and R$^3$ represent hydrogen;
R$^4$ represents hydroxy or oxytrimethylsilyl; and
R$^5$ represents chloro.

4. A compound of claim 3 wherein R$^4$ represents hydroxy and r is 1.

5. A compound of claim 3 wherein R$^4$ represents hydroxy and r is 2.

6. A compound of claim 3 wherein R$^4$ represents oxytrimethylsilyl and r is 1.

7. A compound of claim 3 wherein R$^4$ represents oxytrimethylsilyl and r is 2.

8. A compound of claim 1, having the structure:

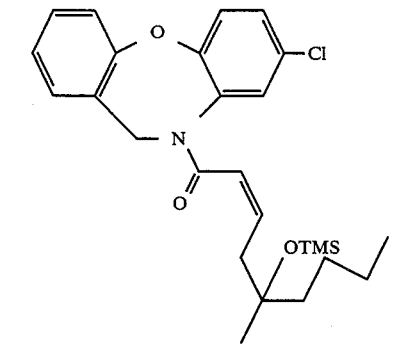

9. A compound of claim 1, having the structure:

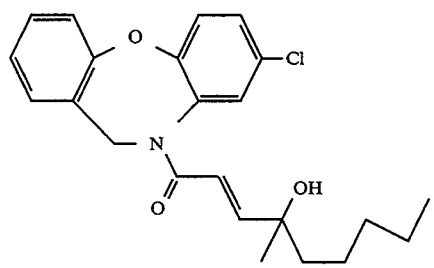

10. A compound of claim 1, having the structure:

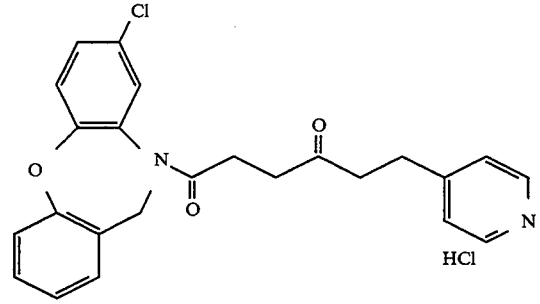

11. A compound of claim 1 wherein the compound is selected from the group consisting of:
8-chloro-10,11-dihydro-10-[5-methyl-1-oxo-5-[(trimethylsilyl)oxy]-2Z-nonenyl]-dibenz[b,f][1,4]oxazepine;
8-chloro-10,11-dihydro-10-[5-methyl-1-oxo-5-[(trimethylsilyl)oxy]-2E-nonenyl]-dibenz 8 b,f][1,4]oxazepine;
8-chloro-10,11-dihydro-10-(5-hydroxy-5-methyl-1-oxo-2E-nonenyl)dibenz[b,f][1,4]oxazepine;
8-chloro-10,11-dihydro-10-[4-methyl-1-oxo-4-[(trimethylsilyl)oxy]-2E-nonenyl]dibenz-[b,f][1,4]oxazepine;
8-chloro-10,11-dihydro-10-(4-hydroxy-4-methyl-1-oxo-2E-nonenyl )dibenz-[b,f][1,4]oxazepine;
8-chloro-10,11-dihydro-10-(4-hydroxy-1-oxo-2E-nonenyl)dibenz[b,f][1,4]oxazepine;
glycine, 1-[3-(8-chloro-10,11-dihydrodibenz-[b,f][1,4]oxazepin-10-yl)-3-oxo-1E-propenyl]-hexyl ester, monohydrochloride;
8-chloro-10,11-dihydro-10-(1,4-dioxo-2E-nonenyl)-dibenz[b,f][1,4]oxazepine;
8-chloro-10,11-dihydro-10-(1-oxo-2E-nonenyl)-dibenz[b,f][1,4]oxazepine;

8-chloro-10,11-dihydro-10-(4-hydroxy-1-oxo-2-nonynyl)dibenz[b,f][1,4]oxazepine; or 8-chloro-10-[1,4-dioxo-6-(4-pyridinyl)hexyl]-10,11-dihydrodibenz[b,f][1,4]-oxazepine, monohydrochloride 12. A pharmaceutical composition comprising a pharmaceutically acceptable carrier and a therapeutically-effective amount of a compound of claim 1.

13. The pharmaceutical composition of claim 12 wherein the compound is selected from the group consisting of:

8-chloro-10,11-dihydro-10-[5-methyl-1-oxo-5-[(trimethylsilyl)oxy]-2Z-nonenyl]-dibenz[b,f][1,4]oxazepine;

8-chloro-10,11-dihydro-10-[5-methyl-1-oxo-5-[(trimethylsilyl)oxy]-2E-nonenyl]-dibenz[b,f][1,4]oxazepine;

8-chloro-10,11-dihydro-10-(5-hydroxy-5-methyl-1-oxo-2E-nonenyl)dibenz[b,f][1,4]oxazepine;

8-chloro-10,11-dihydro-10-[4-methyl-1-oxo-4-[(trimethylsilyl)oxy]-2E-nonenyl ]dibenz-[b,f][1,4]oxazepine;

8-chloro-10,11-dihydro-10-(4-hydroxy-4-methyl-1-oxo-2E-nonenyl)dibenz[b,f][1,4]oxazepine;

8-chloro-10,11-dihydro-10-(4-hydroxy-1-oxo-2E-nonenyl)dibenz[b,f][1,4]oxazepine;

glycine, 1-[3-(8-chloro-10,11-dihydrodibenz[b,f][1,4]oxazepin-10-yl)-3-oxo-1E-propenyl]-hexyl ester, monohydrochloride;

8-chloro-10,11-dihydro-10-(1,4-dioxo-2E-nonenyl)-dibenz[b,f][1,4]oxazepine;

8-chloro-10,11-dihydro-10-(1-oxo-2E-nonenyl)-dibenz[b,f][1,4]oxazepine;

8-chloro-10,11-dihydro-10-(4-hydroxy-1-oxo-2-nonynyl)dibenz[b,f][1,4]oxazepine; or 8-chloro-10-[1,4-dioxo-6-(4-pyridinyl)hexyl]-10,11-dihydrodibenz[b,f][1,4]-oxazepine, monohydrochloride.

14. The pharmaceutical composition of claim 13 wherein the compound is selected from the group consisting of:

8-chloro-10,11-dihydro-10-[5-methyl-1-oxo-5-[(trimethylsilyl)oxy]-2Z-nonenyl]dibenz[b,f][1,4]oxazepine;

8-chloro-10,11-dihydro-10-(4-hydroxy-4-methyl-1-oxo-2E-nonenyl)dibenz-[b,f][1,4]oxazepine; or 8-chloro-10-[1,4-dioxo-6-(4-pyridinyl)hexyl]-10,11-dihydrodibenz[b,f][1,4]-oxazepine, monohydrochloride.

15. A method for treating pain in an animal comprising administering to the animal a therapeutically-effective amount of a compound of claim 1.

16. The method according to claim 15 wherein the compound is selected from the group consisting of:

8-chloro-10,11-dihydro-10-[5-methyl-1-oxo-5-[(trimethylsilyl)oxy]-2Z-nonenyl]-dibenz[b,f][1,4]oxazepine;

8-chloro-10,11-dihydro-10-[5-methyl-1-oxo-5-[(trimethylsilyl)oxy]-2E-nonenyl]-dibenz[b,f][1,4]oxazepine;

8-chloro-10,11-dihydro-10-(5-hydroxy-5-methyl-1-oxo-2E-nonenyl)dibenz[b,f][1,4]oxazepine;

8-chloro-10,11-dihydro-10-[4-methyl-1-oxo-4-(trimethylsilyl)oxy]-2E-nonenyl]dibenz-[b,f][1,4]oxazepine;

8-chloro-10,11-dihydro-10-(4-hydroxy-4-methyl-1-oxo-2E-nonenyl)dibenz-[b,f][1,4]oxazepine;

8-chloro-10,11-dihydro-10-(4-hydroxy-1-oxo-2E-nonenyl)dibenz[b,f][1,4]oxazepine;

glycine, 1-[3-(8-chloro-10,11-dihydrodibenz[b,f][1,4]oxazepin-10-yl)-3-oxo-1E-propenyl]-hexyl ester, monohydrochloride;

8-chloro-10,11-dihydro-10-(1,4-dioxo-2E-nonenyl)-dibenz[b,f][1,4]oxazepine;

8-chloro-10,11-dihydro-10-(1-oxo-2E-nonenyl)-dibenz[b,f][1,4]oxazepine;

8-chloro-10,11-dihydro-10-(4-hydroxy-1-oxo-2-nonynyl)dibenz[b,f][1,4]oxazepine ; or 8-chloro-10-[1,4-dioxo-6(4-pyridinyl)hexy-10,11-dihydrodibenz[b,f][1,4]-oxazepine, monohydrochloride.

17. The method according to claim 15 wherein the compound is selected from the group consisting of:

8-chloro-10,11-dihydro-10-[5-methyl-1-oxo-5-[(trimethylsilyl)oxy]-2Z-nonenyl]-dibenz[b,f][1,4]oxazepine;

8-chloro-10,11-dihydro-10-(4-hydroxy-4-methyl-1-oxo-2E-nonenyl)dibenz-[b,f][1,4]oxazepine; or 8-chloro-10-[1,4-dioxo-6-(4-pyridinyl)hexyl]-10,11-dihydrodibenz[b,f][1,4]- oxazepine, monohydrochloride.

* * * * *

UNITED STATES PATENT AND TRADEMARK OFFICE
CERTIFICATE OF CORRECTION

PATENT NO. : 5,449,673  Page 1 of 3
DATED : September 12, 1995
INVENTOR(S) : Chandrakumar, et al.

It is certified that error appears in the above-indentified patent and that said Letters Patent is hereby corrected as shown below:

Column 1, line 46, reading "as-cholesterol" should read --as cholesterol--.

Column 1, line 66, reading "1(substituted" should read --1-(substituted--.

Column 2, line 5, reading "[1,41" should read --[1,4]--.

Column 3, line 47, reading "2, 139-148" should read --9, 139-148--.

Column 3, line 63, reading "structureactivity" should read --structure activity--.

Column 5, line 64, reading "6membered" should read --6-membered--.

Column 9, line 32, reading "Bergs" should read --Berge--.

Column 13, line 35, should read --ii) isobutyl chloroformate/N,O-dimethyl hydroxylamine. 2) alkyne/n-BuLi.

Column 15, line 38, reading "carbonl" should read --carbonyl--.

Column 17, line 41, reading "retool" should read --mmol--.

Column 17, line 64, reading "lander" should read --under--.

Column 18, line 66, reading "[b,f] 1,4]" should read [b,f][1,4]--.

UNITED STATES PATENT AND TRADEMARK OFFICE
CERTIFICATE OF CORRECTION

PATENT NO. : 5,449,673
DATED : September 12, 1995
INVENTOR(S) : Chandrakumar, et al.

It is certified that error appears in the above-indentified patent and that said Letters Patent is hereby corrected as shown below:

Column 19, line 58, reading "oxazepin" should read --oxazepine--.

Column 22, line 67, reading "tenminute" should read --ten-minute--.

Column 24, line 23, reading "%he" should read --the--.

Column 24, line 45, reading "quantirate" should read --quantitate--.

Column 24, line 60, reading "PBO" should read --PBQ--.

Column 25, line 3, reading "PBO" should read --PBQ--.

Column 26, line 19, reading "i mg" should read --1 mg--.

Column 26, line 55, reading "alphatocopherol" should read --alpha-tocopherol--.

Column 27, line 7, reading "I per cent" should read --1 per cent--.

Column 27, line 51, reading "bentonits" should read --bentonite--.

Column 30, line 29, reading "sealLed" should read --sealed--.

Column 31, line 36, reading "OS" should read --O,S--.

Column 31, line 37, reading "n represents" should read --r represents--.

UNITED STATES PATENT AND TRADEMARK OFFICE
CERTIFICATE OF CORRECTION

PATENT NO. : 5,449,673
DATED : September 12, 1995
INVENTOR(S) : Chandrakumar, et al.

It is certified that error appears in the above-indentified patent and that said Letters Patent is hereby corrected as shown below:

Column 32, line 51, reading "8 b,f]" should read --[b,f]--.

Column 33, line 3, reading "-6(4-" should read -- -6-(4- --.

Column 34, line 33, reading "-6(4-pyridinyl)hexy-" should read -- -6-(4-pyridinyl)hexyl]- --.

Signed and Sealed this

Eighth Day of July, 1997

Attest:

BRUCE LEHMAN

Attesting Officer

Commissioner of Patents and Trademarks